United States Patent [19]
Montgomery

[11] Patent Number: 5,338,312
[45] Date of Patent: Aug. 16, 1994

[54] ARTICLE HAVING MULTI-LAYERED LUBRICANT AND METHOD THEREFOR

[75] Inventor: David B. Montgomery, Cary, N.C.

[73] Assignee: Becton, Dickinson and Company, Franklin Lakes, N.J.

[21] Appl. No.: 955,963

[22] Filed: Oct. 2, 1992

[51] Int. Cl.⁵ .............................................. A61M 5/315
[52] U.S. Cl. ...................................... 604/230; 427/2.3
[58] Field of Search .............. 604/230, 187, 218, 207, 604/12, 172, 263; 427/2, 563, 574, 334; 361/225, 226, 230

[56] References Cited

U.S. PATENT DOCUMENTS

| | | | |
|---|---|---|---|
| 4,767,414 | 8/1988 | Williams et al. | 604/230 |
| 4,844,986 | 7/1989 | Karakelle et al. | 428/447 |
| 5,272,012 | 12/1993 | Opolski | 428/423.1 |

Primary Examiner—C. Fred Rosenbaum
Assistant Examiner—V. Alexander
Attorney, Agent, or Firm—Richard E. Brown

[57] ABSTRACT

An article having surfaces in sliding contact is lubricated at the interface with a multi component system. A first crosslinked basement lubricant is coated onto a surface, such as a syringe barrel. A second lubricant is coated over the crosslinked lubricant. The second surface, such as a syringe stopper is engaged with the first surface. A second aspect of the invention is a method for lubricating an article such as a syringe. A low viscosity prebasement lubricant is evenly coated onto the inside surface of the syringe barrel and then crosslinked by a plasma to a viscous liquid or substantially solid basement lubricant. A second surface lubricant is then applied over the basement lubricant.

10 Claims, 2 Drawing Sheets

ARTICLE HAVING MULTI-LAYERED LUBRICANT AND METHOD THEREFOR

BACKGROUND OF INVENTION

1. Field of Invention

This invention relates to articles having sliding surfaces, and more particularly relates to a lubricating system effective across a maximum range of velocities useful for articles having sliding surfaces.

2. Background

Certain devices require slow and controlled initiation and maintenance of sliding movement of one surface over another surface. It is well known that two stationary surfaces having a sliding relationship often exhibit sufficient resistance to initiation of movement that gradually increased force applied to one of the surfaces does not cause movement until a threshold force is reached at which point a sudden sliding separation of the surfaces takes place. This sudden separation of stationary surfaces into a sliding relationship is generally referred to as breakout, and the stationary period is generally referred to as stick.

Often, immediately after breakout, sliding movement stops and the two surfaces once again go into stick, only to undergo another breakout with time and continued force. The condition of alternating stick and breakout is generally referred to as chatter.

Breakout and chatter are particularly troublesome in liquid dispensing devices using stopcocks, such as burets, pipers, addition funnels and the like where careful dropwise control of flow is desired. The problem of breakout and chatter is most severe in devices, such as syringes, used to deliver small, accurately measured quantities of a liquid by smooth, incremental line-to-line advancement of one surface over a graduated second surface.

Syringes are commonly used either manually, i.e., when stopper advancement is achieved by holding the syringe in the hand and applying finger pressure on the barrel, or automatically, i.e. in conjunction with an infusion pump. Manually operated syringes develop a stopper velocity of from about 20 to 1000 mm per min., and usually are operated at hundreds of mm per min. In the present disclosure, this velocity is referred to as manual velocity.

On the other hand, syringes used with an infusion pump are designed to deliver a medicament over a long period of time. In these devices the syringe stopper travels at ultra slow velocities, from about 0.003 to about 2.0 mm/min. This stopper velocity is hereinafter referred to as the pump velocity.

It will be readily apparent that chatter is most likely to develop when the surfaces must move very slowly relative to each other, i.e., at pump velocity. Further, these velocities cause frictional forces to increase substantially, so that the barrel and stopper are often in stick, during which time no medicament is dispensed for extended periods. When breakout does occur, a bolus may be administered. Subsequent stick followed by breakout leads to chatter.

U.S. Pat. No. 4,767,414 to Williams et al. discloses a method for overcoming breakout for a hand-held syringe. The method includes applying a silicone lubricant to a surface slidably engaged with a second surface and treating both the surface and the silicone with an ionizing plasma.

Karakelle et al., in U.S. Pat. No. 4,844,986 discloses plasma polymerization of a silicon containing monomer and deposition of the polymer on a polypropylene surface so that both the surface and the polymer are crosslinked. This surface is taught to be non-lubricious, but has a surface energy which allows it to be coated evenly with an ordinary polydimethylsiloxane lubricant.

Since off-the-shelf syringes are used both manually and with a pump, there is a need for a lubricant system effective at both manual and pump velocities. This need is fulfilled by the present invention.

SUMMARY OF THE INVENTION

One aspect of the invention is an article having surfaces in sliding contact. The interface between the sliding surfaces is lubricated with a combination of lubricants. One of the surfaces is coated with a galled or crosslinked lubricant of high viscosity, hereinafter called the basement lubricant. A second lubricant of lower viscosity, hereinafter called the surface lubricant, is coated onto the crosslinked lubricant and may also be crosslinked.

The preferred article is a syringe in which the syringe barrel, preferably polypropylene, and a stopper are in sliding contact. The crosslinked basement lubricant may be applied to the barrel and the surface lubricant may be coated onto the basement lubricant.

The preferred basement lubricant is a silicone oil crosslinked to a highly viscous oil or solid. The preferred surface lubricant is also a silicone oil of lower viscosity which may also be crosslinked.

Another aspect of the invention is a method for lubricating the article of the invention. The first surface, preferably the syringe barrel, is coated with a prebasement lubricant. The prebasement lubricant is sufficiently mobile to be spread evenly over the barrel, after which it is crosslinked to give the basement layer. After crosslinking, the surface lubricant is evenly coated onto the basement layer, then optionally lightly crosslinked. The syringe stopper may then be engaged to the barrel.

Syringes are commonly used either manually, in which the stopper travels in the barrel at a high velocity, or with an infusion pump at low velocity. The multicomponent lubricant system of the present invention allows the same off-the-shelf syringe to be used in either mode with smooth stopper advancement, i.e., substantially no stick, chatter or breakout. Prior art lubricating systems are not effective in both modes.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The article of the present invention may be any article which includes two surfaces in sliding contact. For example, a plastic catheter which slides over a metal or plastic cannula during catheter insertion may benefit from lubrication using the disclosed multilayer lubricant system. The preferred article of the invention is a syringe in which the syringe stopper is the first surface and the syringe barrel is the second surface. The invention contemplates a syringe of any size ranging from about 0.1 cc to 100 cc.

Figure 1:
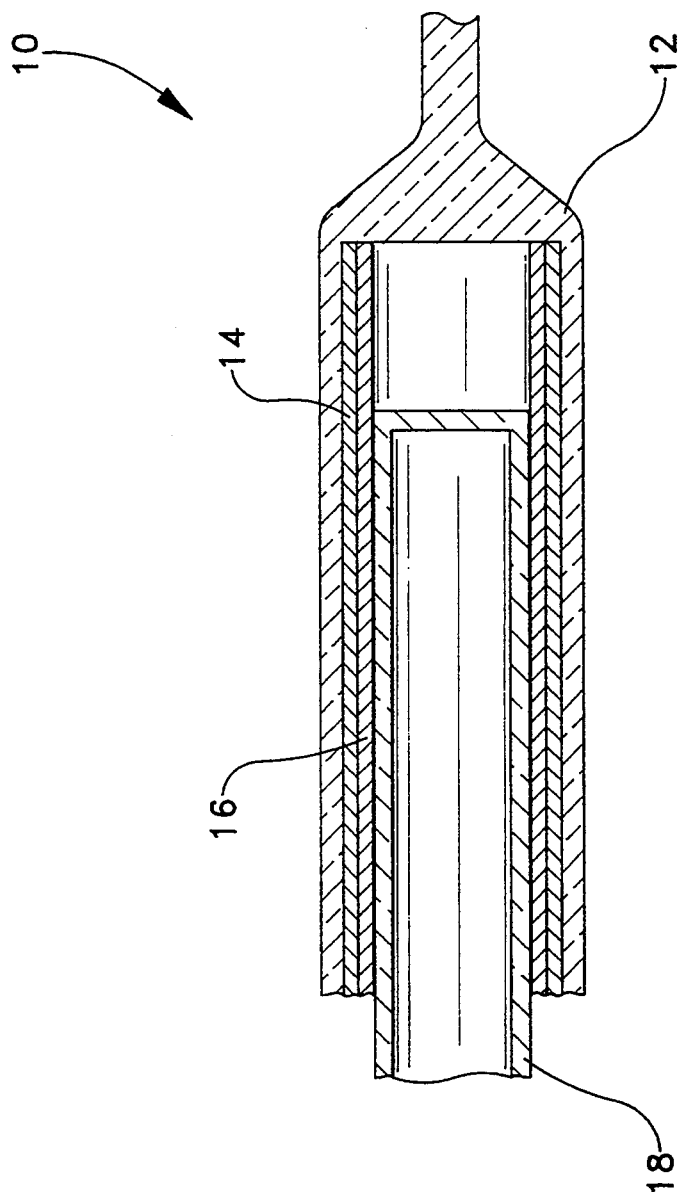
FIG. 1 illustrates a syringe barrel and stopper lubricated in accordance with the invention.

FIG. 1 illustrates the components of the article of the invention in terms of the preferred article, a syringe stopper which travels in a syringe barrel. In FIG. 1, a syringe 10 includes a syringe barrel 12 having a crosslinked basement lubricant 14 on barrel 12. A surface lubricant 16 is over basement lubricant 14. A syringe stopper 18 is slidably engaged to surface lubricant 16.

The two surfaces in sliding contact may be of any material, such as glass, ceramic, metal and preferably plastic. The first surface preferably is a syringe barrel of glass or a polymer such as polyolefin, polystyrene, polyvinyl chloride or polyurethane. The preferred first surface is polypropylene. The preferred second surface may be a polymeric syringe stopper. Preferred stoppers are of elastomeric materials, either thermoplastic or thermoset, as, for example, natural or synthetic rubbers. Many materials suitable for the syringe stopper are commercially available, such as SANTOPRENE TM or KRATON TM synthetic rubbers.

Commercial off-the-shelf syringes may be used at pump or manual velocities. Thus the invention contemplates a lubricant system, effective at all velocities, which is characterized by two or more lubricating components. A first lubricating component, the basement lubricant, provides lubrication at pump velocities and a second lubricating component, the surface lubricant, provides lubrication at manual velocities. Neither the basement lubricant nor the surface lubricant, alone, provides lubrication at all syringe velocities.

The basement layer is a highly crosslinked or gelled material on at least one of the sliding surfaces, preferably on the syringe barrel. A prebasement lubricant, such as a hydrocarbon oil, vegetable oil, peanut oil, mineral oil, wax, grease or preferably a silicone oil may be applied to the surface and crosslinked. The preferred prebasement silicone oil may have a viscosity of about 100 to 100,000, preferably about 1000 to 20,000, most preferably about 12,500 centistokes (cs).

Application of the prebasement material may be carried out by any method which results in a substantially uniform coating. Thus the prebasement material may be wiped, dipped or sprayed onto the surface, or it may be applied as a solution in a solvent such as chloroform or FREON TM TF, after which the solvent may be evaporated. Alternatively, the prebasement material maybe crosslinked prior to being applied to the surface.

Any method may be used for gelling or crosslinking. For example, the prebasement material may be chemically gelled with an agent such as sorbitol or xylitol. Preferably, the prebasement material is crosslinked by treating with an ionizing plasma. A preferred plasma is generated from an oxidative gas, such as air or oxygen. A wide range of power settings, radio frequencies, durations of exposure, temperatures, monomer gas pressures and gas flow rates may be used for plasma generation. Any conventional plasma generating equipment, many of which are commercially available, may be used. Broad ranges for these parameters are; DC or AC power levels up to 200 watts, RF frequency of 0.1 to 50 megahertz; durations of 0.2 to 30 minutes and gas pressures of 0.1 to 5.0 torr. Preferred ranges are 10 to 50 watts, 10 to 20 megahertz, 0.5 to 10 minutes and 0.5 to 3.0 torr.

The degree of gelling or crosslinking of the prebasement material depends on factors which vary with the individual system, such as the nature and surface energetics of the surface materials, the normal forces between the surfaces, the areas of contact between the surfaces, the shape of the leading edge of the stopper and like. In general, crosslinking is carried out until the prebasement material is converted to a viscous liquid or substantially solid gel which remains substantially immobilized on the barrel, i.e. is not scraped up or wiped away but still provides lubrication when the stopper travels at pump velocity in the barrel. The degree of crosslinking may easily be determined experimentally for a given system of surfaces by one skilled in the art.

The thickness of the basement lubricant may be about 0.05 to 2.0, preferably about 0.1 to microns. Thickness does not change to any significant degree when the prebasement material is crosslinked. Thus it is evident that achievement of a suitable basement layer includes selection and adjustment of the thickness and viscosity of the prebasement material and the time of plasma treatment. One skilled in the plasma art may easily determine proper values for the plasma parameters, and further details with respect to these aspect of the invention are not needed for a complete understanding and successful practice of the invention.

It has been found that a syringe in which the barrel-stopper interface is lubricated with a basement lubricant as described above may be used in conjunction with an infusion pump at pump velocities without chatter so that a patient may receive a very slow but continuous administration of medication without bolus.

While the above-described basement lubricant effectively lubricates the barrel-stopper assembly at pump velocities, it is not an effective lubrication system at the manual velocities of hand held syringes because it has too much viscous drag. In order to achieve chatter-free lubrication over the entire velocity range from about 0.003 to about 1000 mm/min, a surface lubricant layer about 0.3 to 10, preferably about 0.8 to 4.0 microns thick may be applied over the basement lubricant. The surface lubricant may preferably be a conventional silicone oil of viscosity about 100 to 60,000, preferably about 1000 to 12,500 cs.

The surface lubricating layer may be applied by any of the conventional methods described above for the prebasement material. The preferred methods for applying the surface lubricant are by spraying or dipping the syringe barrel into a solution, about 4% by weight, of the surface lubricant in a solvent such as chloroform, dichloromethane or preferably a chlorofluorocarbon, such as FREON TM TF.

The surface lubricant may optionally be lightly crosslinked by plasma treatment. A suitable plasma treatment for the surface lubricant may be an oxygen plasma generated using about 10 to 50 watts, about 10–20 megahertz and about 0.1 to 0.4 minutes.

It has been found that, to provide smooth stopper advancement while avoiding chatter at pump velocity and breakout at manual velocity, an Instron force of about 1.6 kg or less, preferably 1.0 kg, may preferably be achieved when using a 60 cc polypropylene syringe equipped with a synthetic rubber stopper. Above about 1.6 kg, chatter results. For a 10 cc syringe, an Instron force above about 0.3 kg causes chatter. For syringes of other sizes, Instron forces providing chatter and breakout-free performance may easily be determined from these values by extrapolation or interpolation.

A syringe lubricated by the procedure disclosed in the aforementioned U.S. Pat. No. 4,767,414, while overcoming breakout and providing smooth movement at the normal velocities resulting from manual advancement of the stopper is subject to increasingly severe chatter at velocities of about 2.0 mm/min and less, as shown in comparative Examples II and V.

On the other hand, lubrication of a barrel-stopper assembly using the system of the aforementioned U.S. Pat. No. 4,844,986 is entirely unsatisfactory. The first layer of the '986 system, taught to be non-lubricious, provides no lubrication at any velocity. The second layer of the '986 system is also not an effective lubricant at low velocities, but is satisfactory at manual velocity.

The following examples are given to further illustrate the invention but are not to be considered as limitative of the invention.

EXAMPLE I

General procedure for syringe lubrication by the method of the invention.

A 60 cc polypropylene syringe barrel was dipped into a 0.5% FREON TM TF solution of a prebasement silicone oil lubricant. The solvent was evaporated and crosslinking was preformed by plasma treatment to give the basement lubricant layer. The barrel was then dipped into a 4% FREON TM TF solution of a surface silicone oil lubricant. This layer was optionally lightly crosslinked by plasma. A SANTOPRENE TM stopper was inserted into the barrel.

A. Basement lubricant resulting from silicone oil of 12,500 centistoke viscosity treated for 30 sec. with an oxygen plasma generated from a power of 40 watts, a frequency of 30 megahertz and a pressure of 0.25 torr.

B. The syringe barrel of A having as the surface lubricant a silicone oil of viscosity 12,500 centistokes.

C. The syringe barrel of B wherein the surface lubricant was lightly crosslinked for 10 sec. with an oxygen plasma generated at 20 watts, 10 megahertz and a pressure of 0.25 Torr.

COMPARATIVE EXAMPLE II

A. A 60 cc polypropylene syringe barrel was lubricated according to Example II of the aforementioned U.S. Pat. No. 4,767,414 and combined with a SANTOPRENE TM stopper.

B. The procedure of A was repeated except a more intense plasma was generated with 12,500 cs silicone oil instead of 100 cs, and an oxygen plasma applied with a quadrupled power density prior to insertion of the stopper.

COMPARATIVE EXAMPLE III

A. A 60 cc polypropylene syringe barrel was plasma coated for 10 min. with hexamethyldisilazane polymer as described in Example I of the afore-mentioned U.S. Pat. No. 4,844,986 and combined with a SANTOPRENE TM stopper.

B. The barrel surface from A was coated with a silicone oil of 12,500 centistoke viscosity as described in U.S. Pat. No. 4,844,986 prior to insertion of the stopper.

COMPARATIVE EXAMPLE IV

A 60 cc polypropylene syringe barrel was lubricated by dipping into a 4% FREON TM TF solution of silicone oil of 12,500 centistoke viscosity, the solvent was removed and a SANTOPRENE TM stopper inserted.

For each syringe of Examples I to IV, the force required to initiate and maintain smooth stopper travel at various stopper velocities was determined with the Instron Model 1122 Universal Testing Machine. The results are given in the TABLE.

TABLE

| Syringe Example | FORCE (kg) STOPPER VELOCITY (mm/min) | | | | |
|---|---|---|---|---|---|
| | 0.05 | 0.2 | 2.0 | 200 | 900 |
| I A | 1.35 | 1.3 | 1.6 | 2.5 | 3.2 |
| B | 1.1 | 1.2 | 0.95 | 0.6 | 0.85 |
| C | 0.85 | 0.95 | 0.8 | 0.55 | 0.9 |
| II A | 2.5 | 2.1 | 1.4 | 0.7 | 1.25 |
| B | 1.25 | 1.15 | 0.7 | 1.8 | 2.3 |
| III A | 8 | 8 | 7 | 15 | immovable |
| B | 3.4 | 2.6 | 2.1 | 0.9 | 1.4 |
| IV | 4.25 | 3.5 | 2.3 | 0.8 | 1.45 |

It is seen from the TABLE that effective lubrication across the entire range of velocities encountered in syringe use is achieved only by the combination of the basement and surface lubricants of the present invention. (I,B and C). Basement lubrication only (IA) fails (chatter) at manual velocities. Syringes lubricated by the prior art methods of the Comparative Examples give satisfactory lubrication at selected low or high velocities but fail at other velocities. None of the prior lubricants is effective at all velocities.

COMPARATIVE EXAMPLE V

Polypropylene syringe barrels of 10 ml capacity were treated as follows:

A. Dipped into 4% FREON TM TF solution of silicone oil of 12,500 centistokes viscosity and the solvent removed.

B. Lubricated in accordance with Example II of U.S. Pat. No. 4,767,414.

C. Lubricated in accordance with Example I, A and B of this disclosure.

Figure 2:
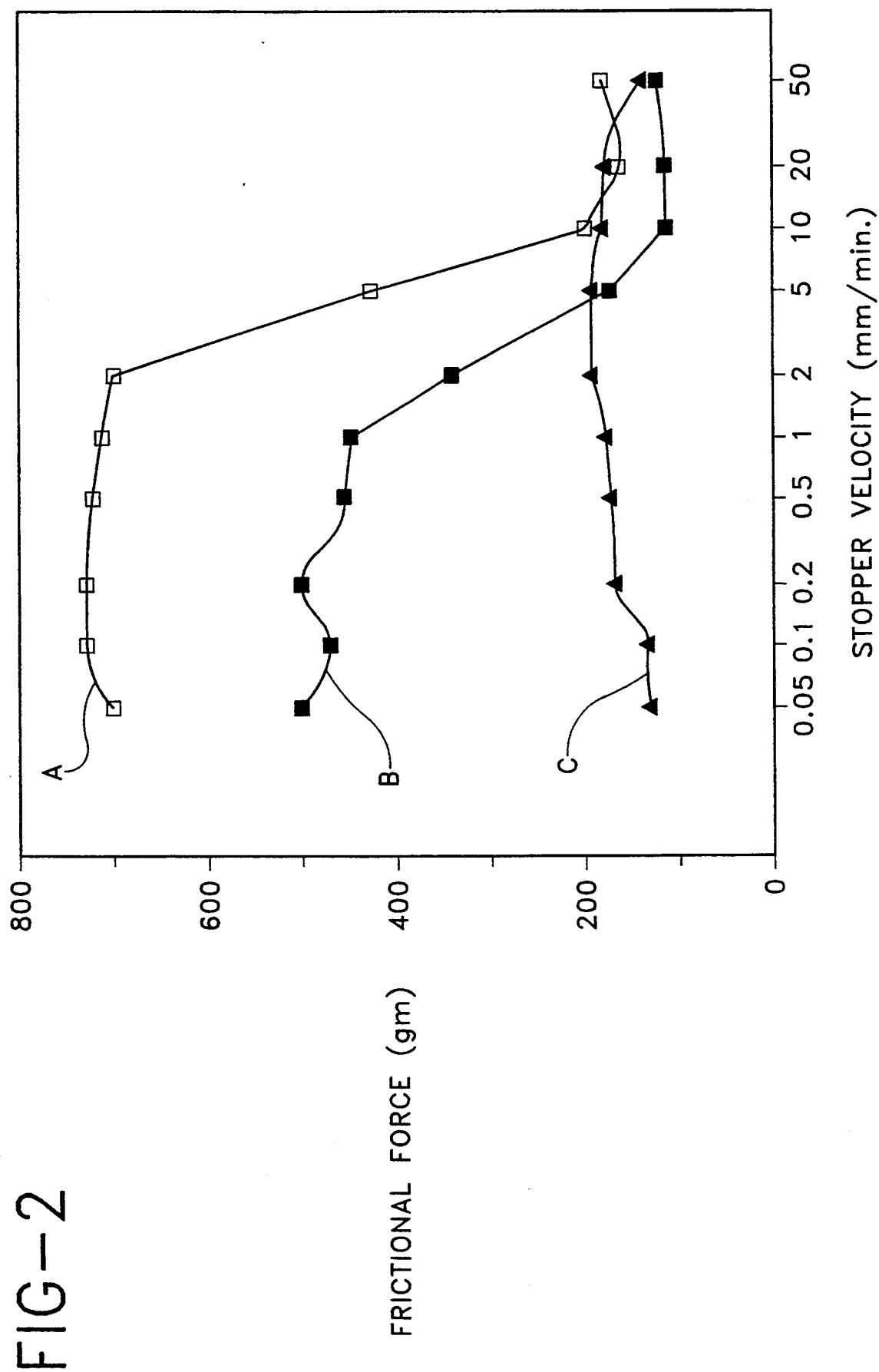
FIG. 2 compares lubrication across a range of stopper velocities for the multi-layered lubricant of the invention and prior art lubricants.

Each syringe was equipped with a KRATON TM stopper and the force required to initiate and maintain smooth stopper travel at various stopper velocities was determined with the Instron Model 1122 Universal Testing Machine. The results are shown in the FIG. 2. It is seen that lubrication via the prior art (A and B) requires high forces which cause chatter at pump velocities. Lubrication in accordance with the invention (C) is accomplished with a uniform force over the range of pump and manual stopper velocities without chatter.

What is claimed is:

1. An article comprising:
    a) a first component having a surface coated with a film of a crosslinked first lubricant;
    b) a film of a second lubricant on said crosslinked lubricant; and
    c) a second component slidably engaged with said first component at an interface between the surfaces whereby said second component is in contact with said second lubricant, said first lubricant remaining substantially immobilized on said first component when said second component is slidably advanced over said second lubricant.

2. A syringe comprising:
    a) a syringe barrel having thereon a film of a crosslinked basement lubricant;

b) a film of a surface lubricant on said crosslinked lubricant; and c) a polymeric syringe stopper slidably located in said barrel and in contact with said surface lubricant, said basement lubricant remaining substantially immobilized on said barrel when said stopper is slidably advanced over said surface lubricant.

3. The syringe of claim 2 wherein said barrel is of a polymer selected from the group consisting of polyolefin, polystyrene, polyvinyl chloride and polyurethane.

4. The syringe of claim 2 wherein said crosslinked lubricant is selected from the group of lubricants consisting of a crosslinked vegetable oil, wax, grease and silicone oil.

5. The syringe of claim 2 wherein said surface lubricant is a silicone oil.

6. The syringe of claim 5 wherein said surface silicone oil lubricant has a viscosity of about 100 to 100,000 centistokes.

7. A syringe comprising:
 a) a polypropylene syringe barrel having thereon a film of a first crosslinked silicone oil basement lubricant;
 b) a film of a second crosslinked silicone oil lubricant having a viscosity of about 1000 to 12,500 centistokes on said basement lubricant, and
 c) a polymeric syringe stopper slidably located in said barrel and in contact with said second silicone oil lubricant, said basement lubricant remaining substantially immobilized on said barrel when said stopper is slidably advanced over said second silicone oil lubricant, said first and second crosslinked silicone lubricants together providing smooth advancement of said stopper in said barrel over a velocity range of about 0.003 to 1000 mm/min.

8. A method for lubricating the interface between a syringe barrel and a syringe stopper comprising:
 a) depositing a layer of a first lubricant on a surface of a syringe barrel;
 b) treating said first lubricant to give a crosslinked first lubricant;
 c) depositing a layer of a second lubricant on the crosslinked first lubricant; and
 d) engaging a syringe stopper in said syringe barrel, said stopper being in contact with said second lubricant, said first lubricant remaining substantially immobilized on said barrel when said stopper is slidably advanced over said second lubricant.

9. The method of claim 8 further comprising plasma treating the second lubricant prior to engaging the syringe stopper and barrel.

10. A method for lubricating the interface between a syringe barrel and a syringe stopper comprising:
 a) depositing a layer of a first silicone lubricant on a syringe barrel;
 b) plasma treating said first silicone lubricant to give a first crosslinked silicon lubricant;
 c) depositing a layer of a second silicone lubricant on the first crosslinked silicone lubricant;
 d) plasma treating said second silicone lubricant to give a second crosslinked silicone lubricant; and
 e) engaging a syringe stopper in said syringe barrel, said stopper being in contact with said second crosslinked silicone lubricant, said first crosslinked silicon lubricant remaining substantially immobilized on said barrel when said stopper is slidably advanced over said second crosslinked silicone lubricant, said first and second crosslinked silicone lubricants together providing smooth advancement of said stopper in said barrel over a velocity range of about 0.003 to 1000 mm/min.

* * * * *